US009585923B2

(12) United States Patent
Lee et al.

(10) Patent No.: US 9,585,923 B2
(45) Date of Patent: Mar. 7, 2017

(54) ANTIOXIDANT, ANTI-INFLAMMATORY OR ANTI-AGING COMPOSITION CONTAINING TAXUS CAMBIUM- OR PROCAMBIUM-DERIVED CELL LINE AS ACTIVE INGREDIENT

(75) Inventors: Dae Hee Lee, Jeonju (KR); Eun Kyong Lee, Iksan (KR); Eun Mi So, Daejun (KR); Young Woo Jin, Jeollabuk-Do (KR)

(73) Assignee: UNHWA CORPORATION, Jeonju-si (KR)

( * ) Notice: Subject to any disclaimer, the term of this patent is extended or adjusted under 35 U.S.C. 154(b) by 571 days.

(21) Appl. No.: 12/992,810

(22) PCT Filed: May 14, 2009

(86) PCT No.: PCT/KR2009/002553
§ 371 (c)(1),
(2), (4) Date: Feb. 1, 2011

(87) PCT Pub. No.: WO2009/139581
PCT Pub. Date: Nov. 19, 2009

(65) Prior Publication Data
US 2011/0117039 A1    May 19, 2011

Related U.S. Application Data

(63) Continuation-in-part of application No. 12/063,929, filed as application No. PCT/KR2006/001544 on Apr. 25, 2006, now Pat. No. 8,017,397.

(30) Foreign Application Priority Data

Oct. 31, 2005   (KR) .................. 10-2005-0103445
May 14, 2008    (KR) .................. 10-2008-0044227

(51) Int. Cl.
| | | |
|---|---|---|
| *A61K 36/00* | (2006.01) | |
| *A61K 36/13* | (2006.01) | |
| *A61K 8/97* | (2006.01) | |
| *A61Q 19/02* | (2006.01) | |
| *A61Q 19/08* | (2006.01) | |

(52) U.S. Cl.
CPC ............... *A61K 36/13* (2013.01); *A61K 8/97* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 4,795,742 A * | 1/1989 | Liu ................................ 514/26 |
| 5,413,928 A * | 5/1995 | Weathers ............... C12P 17/181 424/770 |
| 8,790,927 B2 * | 7/2014 | Park ....................... A61K 36/13 435/410 |
| 2002/0013298 A1 * | 1/2002 | Hunter ......................... 514/113 |
| 2002/0114853 A1 * | 8/2002 | Krasutsky .......... B01D 11/0203 424/725 |
| 2008/0075794 A1 | 3/2008 | Bae |
| 2008/0188924 A1 * | 8/2008 | Prabhu ....................... 623/1.16 |
| 2009/0196933 A1 * | 8/2009 | De ....................... A61K 9/0019 424/491 |
| 2010/0272692 A1 * | 10/2010 | Park ..................... A61K 36/13 424/93.7 |

FOREIGN PATENT DOCUMENTS

| KR | 10-2003-0007997 | 1/2003 | |
| KR | 10-2004-0050324 | 6/2004 | |
| WO | 93-17121 A1 | 9/1993 | |
| WO | 97-44476 A1 | 11/1997 | |
| WO | WO2007052876 | * 5/2007 | ............... C12N 5/04 |

OTHER PUBLICATIONS

Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Wikipedia: Taxus; Online, URL<http://en.wikipedia.org/wiki/Taxus> accessed Jun. 25, 2013, 4 pages.*
Smet et al. Herbal Remedies; The New England Journal of Medicine; Dec. 19, 2002, vol. 347, Issue 25, p. 2046, 11 pages.*
Spjut, R. Overview of the Genus *Taxus* (Taxaceae): The Species; Their Classification, and Female Reproductive Morphology; 2010; World Botanical.com; Online, URL<http://www.worldbotanical.com/TAXNA.HTM>, accessed Jun. 25, 2013, 18 pages.*
Bogdan C., Nat. Immunol., 2:907, 2001.
Chen, Ann. N.Y. Acad. Sci., 908:111, 2000.
Chen Q. et al., Proc. Natl. Acad. Sci. U.S.A. May 9; 92(10):4337, 1995.
Chung H.Y. et al., Kor. J. Gerontol., 2:1, 1992.
Finkel & Holbrook, Nature, 408(6809); 239, 2000.
Finkel, T. & Holbrook, N.J., Science 408; 239, 2000.
Fridovich L., Science, 201:175, 1978.
Fukuzawa et al., J. Act. oxyg. Free Rad., 1:55, 1990.
Gey et al., Am. Ac. J. Cin. Nutr., 53:326, 1991.
Halliwell et al., Drugs, 42:569, 1991.
Hatano et al., Natural Medicines, 49:359, 1995.
Hayflick & Moorehead P.S., Exp. Cell Res., 25:585, 1961.
Lesnefsky, E.J. & Hoppel, C.L. Arch. Biochem. Biophys. 420, 287, 2003.

(Continued)

*Primary Examiner* — Chris R Tate
(74) *Attorney, Agent, or Firm* — Tristan A. Fuierer; Moore & Van Allen, PLLC

(57) ABSTRACT

The present invention relates to an antioxidant, anti-inflammatory or anti-aging composition containing any one or more of a *Taxus* cambium- or procambium-derived cell line, an extract thereof, a lysate thereof and a culture medium thereof. The composition according to the present invention has minimized side effects compared to existing antioxidants and anti-inflammatory agents, is involved in intracellular metabolism to reduce intracellular reactive oxygen species, and reduces and induces aging-related signals. Thus, the composition of the preset invention is useful for preventing and delaying aging. In addition, the composition of the present invention has the effect of inhibiting melanogenesis, and thus is useful as a whitening cosmetic composition.

16 Claims, 13 Drawing Sheets

(56) References Cited

OTHER PUBLICATIONS

Masaki et al., Biol. Pharm. Bull, 18:162, 1995.
Packer L. & Fuehr K., Nature, 267(5610); 423, 1977.
Regnstrom et al., Lancet., 16:1183, 1992.
Thomas C. & Squier, Experimental Gerontology, 36; 1539, 2001.
Gong et al., "Nitric oxide mediates inactivation of glutathione S-transferase in suspension culture of Taxus cuspidata during shear stress," Jrl. of Biotech., 2006, vol. 123, pp. 185-192.
International Search Report for PCT/KR2009/002553, mailed Oct. 27, 2009.

\* cited by examiner

ANTIOXIDANT, ANTI-INFLAMMATORY OR ANTI-AGING COMPOSITION CONTAINING TAXUS CAMBIUM- OR PROCAMBIUM-DERIVED CELL LINE AS ACTIVE INGREDIENT

CROSS-REFERENCES TO RELATED APPLICATIONS

This application is a continuation-in-part of U.S. patent application Ser. No. 12/063,929, filed on Feb. 15, 2008, and entitled "Isolated Population of Plant Single Cells and Method of Preparing Same, now U.S. Pat. No. 8,017,397, issued on Sep. 13, 2011, which is a U.S. National phase application, pursuant to 35 U.S.C. §371, of PCT/KR2006/001544, filed Apr. 25, 2006, which claims priority to Korean Application No. 10-2005-0103445, filed Oct. 31, 2005. In addition, this application is a U.S. National Phase application, pursuant to 35 U.S.C. §371 of International Patent Application No. PCT/KR2009/002553, filed May 14, 2009, which claims priority to Korean Application No. 10-2008-0044227, filed May 4, 2008. The entire contents of International Patent Application No. PCT/KR2009/002553 and Korean Application No. 10-2008-0044227 are incorporated herein by this reference.

TECHNICAL FIELD

The present invention relates to an antioxidant, anti-inflammatory or anti-aging composition containing any one or more of a *Taxus* cambium- or procambium-derived cell line, an extract thereof, a lysate thereof and a culture medium thereof.

BACKGROUND ART

Aging is a functional, structural and biochemical process that occurs continuously throughout the life of human beings. Aging occurs throughout the cells and tissues of the human body, displays a decrease in metabolic rate, an increase in diseases, a decrease in adaptability and the like, and ultimately leads to the death of the cells and the whole of tissues of the human body. Theories explaining the processes and causes of aging are broadly divided into the genetic theories (Chung. H. Y. et al., *Kor. J. Gerontol.*, 2:1, 1992) and the wear-and-tear theories (Chung. H. Y. et al., *Kor. J. Gerontol.*, 2:1, 1992). The wear-and-tear theories suggest that the cells of organisms lose their functions with the passage of time or due to the accumulation of harmful substances. Among these explanations, the most plausible theory is the free radical theory suggesting that free radicals which are produced through human metabolic processes, radiation exposure, viruses, heavy metals and air pollution form highly toxic substances, thereby stimulating aging and causing various diseases related to aging.

Free radicals are substances having one unpaired electron in the outermost orbit and their structure is highly unstable and reactive because they tend to be stabilized by receiving electrons. Particularly, free radicals which are derived from oxygen are termed "reactive oxygen species", and these reactive oxygen species react with proteins, lipids, carbohydrates and the like to cause lipid peroxidation, DNA damage, protein oxidation and the like, thereby causing damage intracellular structures and ultimately causing the death of cells. Particularly, these reactive oxygen species increase arterosclerosis, Alzheimer's disease and blood homocysteine levels by involving inflammatory processes as a cause of vascular aging.

Oxygen-related toxic substances in the human body are referred to as reactive oxygen species (ROS). Examples of ROS include free radicals, such as superoxide, hydroxyl, peroxyl, alkoxyl and hydroperoxyl, and non-free radial radicals, such as hydrogen peroxide, hypochlorous acid, ozone, singlet oxygen, and peroxynitrite. Among these reactive oxygen species, superoxide free radicals have been most frequently studies and play an important role (Fridovich L., *Science*, 201:175, 1978).

During the progression of aging, ROS generated in cellular mitochondria becomes a target indicating oxidative damage (Lesnefsky, E. J. & Hoppel, C. L. *Arch. Biochem. Biophys.* 420, 287, 2003). There are many reports that the free radical theory regarding intracellular oxygen radicals has much correlation with aging-related oxidative stress and aging-related diseases caused thereby (Finkel, T. & Holbrook, N. J., *Science* 408; 239, 2000) and there are also reports that such oxidative stress play an important role in inducing senescence (Chen Q. et al., *Proc. Natl. Acad. Sci. U.S.A.* May 9; 92(10):4337, 1995; Packer L. & Fuehr K., *Nature*, 267(5610):423, 1977). Such oxidative stress is a term used to describe damage to cells caused by the oxidation of macromolecules by an increasing level of reactive oxygen species and reduced antioxidant reserve (Thomas C. & Squier, *Experimental Gerontology,* 36; 1539, 2001).

Aged cells which are in the progression of replicative senescence can produce ROS at higher levels compared to young cells and also produce toxic byproducts, such as superoxide, hydrogen peroxide, hydroxyl radicals and the like during a normal metabolic process. According to the results of experiments on old individuals or old test animals, tissues accumulate oxidative damage to their DNAs, proteins and lipids (Chen, *Ann. N. Y. Acad. Sci.*, 908:111, 2000). ROS, and particularly, hydroxyl radical, attacks DNA and causes the formation of 8-oxo-2'-deixyguanosine and other potent mutagenic adducts, and the ratio of ROS in each species is associated with life-span and that means it is the decisive factor in defining the rate of aging and various diseases related to aging (Finkel & Holbrook, *Nature,* 408 (6809): 239, 2000).

In 1961, Hayflick and Moorhead first reported that the replicative potential of young cultured cells decreases as the number of divisions increase, and ultimately the cells lose proliferative potential and have a "doubling limited" which the growth condition is over. Since then, ROS has been used to define the senescence-related molecular changes of human cells as experimental models for in vitro senescence and intracellular senescence in human fibroblasts (HAYFLICK L. & MOORHEAD P. S., *Exp. Cell Res.,* 25: 585, 1961).

All aerobic organisms, including humans, fundamentally have a self-defense mechanism against injury caused by reactive oxygen species which always occur during an energy metabolic process that uses oxygen, the production of reactive oxygen species exceeding the defense capability of tissues causes various adult diseases, including arthritis, disorders of the cardiovascular system, and dementia (Halliwell et al., *Drugs,* 42:569, 1991; Fukuzawa et al., *J. Act. oxyg. Free Rad.,* 1:55, 1990).

Reactive oxygen species which are frequently called harmful oxygen species include superoxide anion ($O^{2-}$) which is singlet oxygen produced by oxidation-reduction of the most stable triplet oxygen ($3O_2$); hydrogen peroxide ($H_2O_2$), hydroxyl radical (.OH) as unpaired free radicals, and these cause diseases by damaging factors of the immune system, such as proteins, DNA, enzymers and T cells (Regnstrom et al., *Lancet.*, 16:1183, 1992; Gey et al., *Am. Ac. J. Clin. Nutr.*, 53:326, 1991).

For this reason, studies on the development of antioxidants have been actively conducted and, as a result, many antioxidants are known, including preventive antioxidant enzymes, such as superoxide dismutase, catalase and glutathioneperoxidase, natural antioxidants, such as vitamin E, vitamin C, carotenoid and glutathione, and synthetic antioxidants, such as t-butyl-4-hydroxyanisole (BHA) and 3,5-(t-butyl)-4-hydroxytoluene (BHT). However, the antioxidant enzymes show a decrease in the defense ability against reactive oxygen species as people get older, and the synthetic antioxidants are known to have mutagenecity and toxicity. For these reasons, it is urgently required to develop more stable and potent natural antioxidants (Hatano et al., *Natural Medicines*, 49:359, 1995; Masaki et al., *Biol. Pharm. Bull*, 18:162, 1995).

Meanwhile, inflammation is a local response which appears against injury sites to initiate the removal of invasion of pathogens or damaged tissues. Despite its positive role, inflammation became one of the most general pathogenic mechanisms for human diseases. The production of nitric oxide (NO) in activated monocytes and macrophages initiates a potent inflammatory response and is most important in an initial immune response to bacterial pathogens (Bogdan C., *Nat. Immunol.*, 2:907, 2001).

When there is a damage to a tissue (cell) or an infection by a foreign substance (e.g., bacteria, fungi, viruses, various allergy-inducing materials), it usually entails an inflammatory response expressed as a series of complex physiological responses such as activation of enzyme, secretion of inflammation-mediating materials, infiltration of body fluid, cell movement, and damage to tissues that are related to various inflammation-mediating factors and immunocytes in local blood vessels and body fluid, and as external symptoms such as erythema, edema, pyrexia and pain. For normal persons, inflammatory responses remove external sources of infection, reproduce damaged tissues, and recover the function of organisms, but when an antigen is not removed or inflammatory responses occur excessively or continuously due to intrinsic substances, inflammatory responses stimulate damage to mucosa and, as a result, in some cases, cause diseases such as cancer. Accordingly, there has been a need to develop natural anti-inflammatory agents which can prevent excessive and continuous inflammatory responses without causing side effects.

Therefore, the present inventors have made many efforts to develop natural material-derived compositions which minimized side effects compared to existing antioxidants and anti-inflammatory agents and have excellent antioxidant activity and anti-inflammatory activity. As a result, the present inventors have found that a *Taxus* cambium- or procambium-derived cell line and an extract thereof have excellent inhibitory effects against aging and inflammation, thereby completing the present invention.

DISCLOSURE OF INVENTION

It is an object of the present invention to a natural material-derived composition which has minimized side effects compared to existing antioxidants and anti-inflammatory agents and shows antioxidant and anti-inflammatory activities and the effects of preventing and delaying aging.

To achieve the above object, the present invention provides an antioxidant, anti-inflammatory or anti-aging composition containing any one or more of a cell line, which is derived from a *Taxus* cambium or procambium and has the following characteristics, an extract thereof, a lysate thereof and a culture medium thereof:

(a) it is in an innately undifferentiated state;
(b) it has a growth rate higher than those of cell lines derived from tissues other than the cambium or procambium of *Taxus* and is cultured stably; and
(c) it is morphologically characterized by a number of vacuoles.

The present invention also provides an anti-aging cosmetic composition containing any one or more of said cell line, an extract thereof, a lysate thereof and a culture medium thereof.

The present invention also provides a whitening cosmetic composition containing any one or more of said cell line, an extract thereof, a lysate thereof and a culture medium thereof.

The present invention also provides an antioxidant functional food containing any one or more of said cell line, an extract thereof, a lysate thereof and a culture medium thereof.

The present invention also provides an anti-aging functional food containing any one or more of said cell line, an extract thereof, a lysate thereof and a culture medium thereof.

Other features and embodiments of the present invention will be more fully apparent from the following detailed description and appended claims.

DETAILED DESCRIPTION OF EMBODIMENTS

Figure 1:
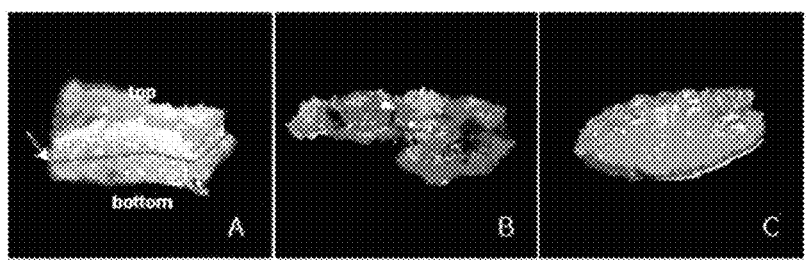
FIG. 1 is a set of photographs showing a process of deriving a cell line according to the present invention, the appearance of cambium or procambium after isolation, and a comparison between de-differentiated cells and *Taxus* cambium- and procambium-derived cells.
Figure 1:
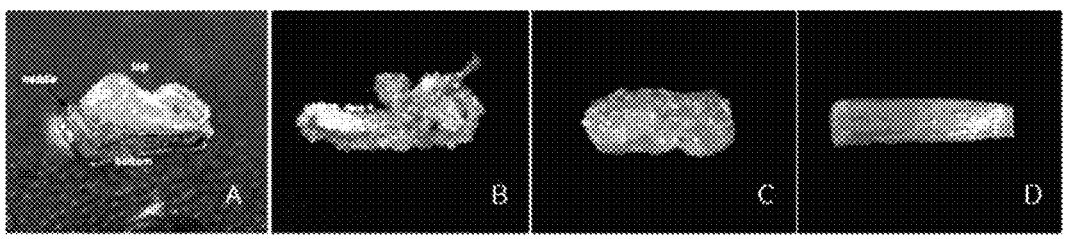
Figure 1:
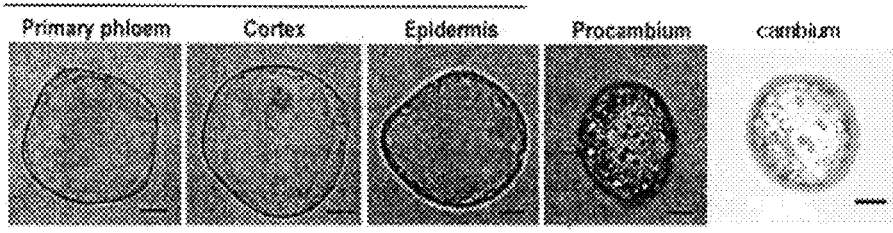

Unless otherwise defined, all technical and scientific terms used herein have the same meaning as commonly understood by one of ordinary skill in the art. Generally, the nomenclature used herein are well known and conventionally used in the art.

The definition of main terms used in the detailed description of the invention is as follows.

Vascular bundle cambium is a lateral meristem that is located on the sides of the plant. The thickening growth of plants occurs by the activity of the cambium; as a result, giant plants having more than 11,000 years of the growth rings may exist. Embryologically, the vascular bundle cambium originates from the procambium, and thus is the same meristem which has been gradually differentiated with meristematic continuity. Such cambium and procambium are 1 phase meristem, and thus in the present invention, it was expected that the use of such cambium and procambium would provide the same effect.

As used herein, the term "lysate" refers to a cell lysate obtained by disrupting cells through a chemical method with, for example, using a detergent, or a physical method. The term "extract" of a cell line refers to a substance obtained by dissolving cells in a solvent and isolating the cells, and the extract can be concentrated through distillation or evaporation. Also, the term "culture medium" of a cell line refers to a cell medium solution from which cells have been removed after culturing the cells.

As used herein, the term "innately undifferentiated" means that cells are not present in an undifferentiated state through a dedifferentiation process, but are originally maintained in a pre-differentiated state.

In one aspect, the present invention relates to an antioxidant, anti-inflammatory or anti-aging composition containing any one or more of a *Taxus* cambium- or procambium-derived cell line, an extract thereof, a lysate thereof and a culture medium thereof.

The *Taxus* cambium- or procambium-derived cell line according to the present invention has the following characteristics: (a) it is an innately undifferentiated state; (b) it has a growth rate higher than those of cell lines derived from tissues other than the cambium or procambium of *Taxus* and is cultured stably; and (c) it is morphologically characterized by a large number of vacuoles. The *Taxus* cambium- or procambium-derived cell line according to the present invention is additionally characterized in that: (a) it is present as single cells during suspension culture; and (b) it has low sensitivity to shear stress in a bioreactor compared to cell lines derived from tissues other than the cambium or procambium of *Taxus*.

The cell line according to the present invention may be obtained using an isolation method comprising the steps of: (a) obtaining a *Taxus* cambium- or procambium-containing tissue; (b) culturing the obtained *Taxus* cambium- or procambium-containing tissue to induce a cambium or procambium layer proliferated from the cambium or procambium and an amorphous callus layer proliferated from tissues other than the cambium or procambium; and (c) isolating a cambium or procambium layer from the callus layer, and collecting a *Taxus* cambium- or procambium-derived cell line from the cambium or procambium layer.

In the present invention, the cell line is preferably additionally cultured in a medium, which contains 3-5 wt % of raw sugar or sugar and at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate. Herein, the methyl jasmonate is preferably contained in an amount of 10~100 μM.

In the present invention, the extract is preferably obtained using a solvent selected from the group consisting of distilled water, alcohol, acetone, DMSO (dimethyl sulfoxide), and mixed solvents thereof.

In the present invention, diploid fibroblasts were treated with the cell line extract together with $H_2O_2$, and as a result, it was found that the cell line extract inhibited the production of reactive oxygen species and the expression of p-ERK½ and induced the expression of MnSOD, suggesting that the cell line extract according to the present invention had antioxidant activity. Also, in the present invention, diploid fibroblasts were treated with the cell line extract together with LPS, and as a result, it was found that the cell line extract according to the present invention inhibited ICAM-1, MMP9, MMP2 and IL-1β, suggesting that the cell line extract had anti-inflammatory activity. Namely, it was found that the cell line extract blocked these signals in the cells, when the cells were treated with the cell line extract before aging and inflammation were induced.

Also, in another Example of the present invention, it was found that the cell line extract and cell line culture medium according to the present invention had the effect of removing reactive oxygen species generated by UV irradiation.

Accordingly, it was found as described above that the cell line extract had antioxidant activity, anti-inflammatory activity and anti-aging activity. Thus, even though in the present invention, there is no specific example showing that a composition containing the cell line shows antioxidant activity, anti-inflammatory activity and anti-aging activity, it will be obvious to those skilled in the art that the composition containing the cell line according to the present invention or a lysate thereof can also show antioxidant activity and anti-inflammatory activity, suggesting that the composition can prevent aging and prevent and relieve skin inflammation.

An antioxidant, anti-inflammatory or anti-aging composition containing, as an active ingredient, any one or more of the cell line according to the present invention, an extract thereof, a lysate thereof and a culture medium thereof, may be provided as a pharmaceutical composition containing any one or more of them alone or in combination with at least one pharmaceutically acceptable carrier, excipient or diluent. The cell line or the cell line extract may be contained in a pharmaceutical composition in a pharmaceutically effective amount depending on disease and its severity, the patient's age, weight, health condition and sex, the route of administration and the period of treatment.

As used herein, the term "pharmaceutically acceptable" refers to a composition that is physiologically acceptable and does not cause gastric disorder, allergic reactions such as gastrointestinal disorder or vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The formulation may be in the form of powders, granules, tablets, emulsions, syrups, aerosols, soft or hard gelatin capsules, sterile injection solutions, sterile powders, etc.

Meanwhile, in another Example of the present invention, it was found that the extract and culture medium of the cell line according to the present invention showed an excellent effect of inhibiting the production of matrix metalloproteinase-1 (MMP-1), compared to a Taxus extract and RA (retionic acid) known to have excellent ant-aging effects, suggesting that a composition containing the cell line according to the present invention, an extract thereof, a lysate thereof or a culture medium thereof has the effect of inhibiting the degradation of collagen, and thus has the effects of preventing skin aging and reducing wrinkles. Thus, the composition is very useful as an anti-aging cosmetic composition. Accordingly, in another aspect, the present invention relates to an anti-aging cosmetic composition containing, as an active ingredient, any one or more of the Taxus cambium- or procambium-derived cell line, an extract thereof, a lysate thereof and a culture medium thereof.

In another Example of the present invention, it was found that the cell line extract and cell line culture medium according to the present invention had the effect of inhibiting melanogenesis in the murine melanoma cell line, suggesting that a composition containing the cell line extract or the cell line culture medium is very useful as a whitening cosmetic composition. Accordingly, in another aspect, the present invention relates to a whitening cosmetic composition containing any one or more of the Taxus cambium- or procambium-derived cell line, an extract thereof, a lysate thereof and a culture medium thereof.

As used herein, the term "functional cosmetic product" refers to a cosmetic product, the functionality of which has been improved by adding thereto one or more of the cell line according to the present invention, an extract thereof, a lysate thereof and a culture medium thereof. For example, the anti-aging cosmetic composition containing the cell line of the present invention or the extract thereof may be used to prepare a functional cosmetic product.

The cosmetic composition of the present invention may contain conventional ingredients for cosmetics, in addition to the cell line extract as an active ingredient. For example, the cosmetic composition may contain conventional auxiliaries such as solvent, stabilizers, solubilizing agents, emulsifier, vitamins, pigments and perfumes, as well as carriers.

The cosmetic composition of the present invention may be prepared into any formulations that are conventional in the art. Preferably, the cosmetic composition can be prepared into a formulation selected from the group consisting of skin lotion, nourishing lotion, nourishing cream, massage cream, nourishing essence, pack, makeup base, foundation, body oil, hair oil, shampoo, and rinse.

Without regard to the examples of cosmetic formulation, the cosmetic composition of the present invention, which contains any one or more of the cell line of the present invention, an extract thereof, a lysate thereof and a culture medium thereof, has an antioxidant effect, and thus has the effects of eliminating free radicals generated in the skin and protecting intracellular antioxidant systems. Accordingly, the cosmetic composition of the present invention can exhibit the effects of preventing and delaying skin aging resulting from oxidation caused by the action of free radicals, and can inhibit the production of MMP-1, thereby preventing skin aging and reducing wrinkles.

In another aspect, the present invention relates to an antioxidant functional food containing, as an active ingredient, any one or more of the Taxus cambium- or procambium-derived cell line, an extract thereof, a lysate thereof and a culture medium thereof.

In still another aspect, the present invention relates to an anti-aging functional food containing, as an active ingredient, any one or more of the Taxus cambium- or procambium-derived cell line, an extract thereof, a lysate thereof and a culture medium thereof.

As used herein, the term "functional food" refers to a food, the functionality of which has been improved by adding thereto the cell line of the present invention or the extract of the cell line.

EXAMPLES

Hereinafter, the present invention will be described in further detail with reference to examples. It is to be understood, however, that these examples are for illustrative purposes only and are not to be construed to limit the scope of the present invention.

Particularly, although the antioxidant, anti-inflammatory and anti-aging effects and whitening effects of an extract and culture medium of a Taxus cambium- or procambium-derived cell line were confirmed in the following examples, it will be obvious to those skilled in the art that the use of the cell line itself can provide the same results as those obtained using the extract or culture medium thereof.

Example 1

Preparation of *Taxus* Cambium- or Procambium-Derived Cell Line (1) Preparation of Plant Material Each of the twig and stem of *Taxus* was collected, and then immediately soaked in 100 mg/L of the antioxidant L-ascorbic acid (DUCHEFA, The Netherlands). Then, they were transported and stored.

Then, the plant was pretreated with a mixed solution of 1% benomyl (Dongbu Hannong Chemical, Korea), 1% daconil (Dongbu Hannong Chemical, Korea), 1% sterptomycin sulphate (DUCHEFA, The Netherlands) and 0.1% cefotaxime sodium (DUCHEFA, The Netherlands) for 24 hours, and then washed with tap water for 30 minutes to remove phenolic compounds and the remaining chemicals. Next, the plant was surface-sterilized in 70% ethanol (DC Chemical, Korea) for 1 min, 30% hydrogen peroxide (LG Chemical, Korea) for 15 min, 1% CLOROX solution for 15 min and 3% CLOROX solution for 5 min, and then washed 3-4 times with water.

(2) Isolation of Procambium and Cambium Tissues from Twig and Stem

The outer tissues of the twig and stem, which have undergone the sterilization process above, were readily peeled by pulling them in the lengthwise direction. The peeled tissues were composed of xylem, procambium or cambium, phloem, cortex and epidermis, and they were cultured in such a manner that the innermost tissue of the peeled tissues, that is, xylem, came into contact with a medium.

(3) Derivation of *Taxus* Procambium- and Cambium-Derived Cell Line

At 4-7 days of initial culture, the division of cells was visually observed from procambium and cambium, and after 15 days of culture, An amorphous callus formed by dedifferentiation started to be induced from the layer composed of phloem, cortex and epidermis. However, cell division in xylem did not occur throughout the culture period, and thus the cambium layer was naturally separated from the xylem. After 30 days of culture, the tissue started to be separated into a cambium layer and a phloem-containing upper layer, that is, an amorphous callus layer ((a) A and (b) A of FIG. 1), and after the tissue has been naturally completely separated into the two layers, the layers were separately cultured in different Petri dishes ((a) B~C and (b) B~D of FIG. 1). In FIG. 1(a) A, the isolation of procambium is shown, the top indicates a phloem/cortex/epidermis-containing tissue, and the bottom indicates procambium. In FIG. 1(b), "A" indicates the isolation of cambium, and the top indicates a phloem/cortex/epidermis-containing tissue, the medium indicates cambium, and the bottom indicates xylem, because the culture was occurred after the removal of xylem. Also, the arrow head indicates the separation between the procambim/cambium layer and the phloem/cortex/epidermis-containing tissue. In FIGS. 1(a) and 1(b), "B" indicates a phloem/cortex/epidermis-containing tissue-derived cell line, which proliferated irregularly due to the difference in division between above cells, "C" indicates a procambium/cambium-derived cell line, which proliferated to form a uniform cell layer through regular cell division, and "D" in 1(b) indicates xylem in which cell division did not occur. After the tissue has been isolated as described above, the white and friable portion thereof having good growth rate was subcultured in the same fresh medium as induction medium at an interval of 21 days.

Meanwhile, the medium used to induce only the procambium- and cambium-derived cell lines is shown in Table 1 below.

TABLE 1

Medium for inducing cell lines from *Taxus* spp. (medium 1)

| | Composition | Contents(mg/L) |
|---|---|---|
| Inorganic salts | $KNO_3$ | 2500 |
| | $(NH_4)_2SO_4$ | 134 |
| | $MgSO_4 \cdot 7H_2O$ | 121.56 |
| | $MnSO_4 \cdot 4H_2O$ | 10 |
| | $ZnSO_4 \cdot 7H_2O$ | 2 |
| | $CuSO_4 \cdot 5H_2O$ | 0.025 |
| | $CaCl_2 \cdot 2H_2O$ | 113.23 |
| | KI | 0.75 |
| | $CoCl_2 \cdot 6H_2O$ | 0.025 |
| | $NaH_2PO_4 \cdot H_2O$ | 130.44 |
| | $H_3BO_3$ | 3 |
| | $Na_2MoO_4 \cdot 2H_2O$ | 0.25 |
| | FeNaEDTA | 36.7 |
| Vitamin | Myo-inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 75 |
| | Proline | 115 |
| Hormone | α-Naphtalene acetic acid | 2 |
| Sucrose | | 10,000 |
| Activated charcoal | | 100 |
| Gelrite | | 2,000 |

The growth regulator auxin such as NAA or IAA was added to the medium at a concentration of 1-3 mg/L, preferably 2 mg/L. The culture was carried out in a dark room controlled at 25±1° C.

For comparison, *Taxus* embryo and needle explants were sterilized, and then cultured in the medium of Table 1. As a result, it was observed that the embryo and needle explants formed callus by dedifferentiation. The callus induced from the embryo and needle explants had an irregular shape due to the difference in division rates between various cells like the case of the phloem-containing tissue, showed unstable growth rate and readily turned brown. The browned and aggregated callus induced from the embryo and needle explants showed slow growth due to phenolic compounds secreted therefrom, and ultimately died. Namely, after 6 months of culture, the calluses induced from the embryo and needle explants were difficult to maintain and culture. However, the procambium- and cambium-derived cells were stably maintained without variations in their growth rates, growth patterns and aggregation degrees, when they were cultured for a long period of more than 20 months, suggesting that the large scale cell culture would be possible.

(4) Observation of Growth Phases and Characteristics of Isolated Cell Lines

The procambium- and cambium-derived cell lines were placed in a flask containing the liquid medium shown in Table 2 below. Then, the cell lines in the flask were cultured in a rotating shaker under dark conditions at 100 rpm at 25±1° C. The interval of subculture was set at 2 weeks, such that the cultured cells could always be maintained in high viability in the exponential growth phase.

TABLE 2

Suspension medium in *Taxus* spp. (medium 2)

| | Composition | Contents(mg/L) |
|---|---|---|
| Inorganic salts | Ca(NO$_3$)$_2$ | 471.26 |
| | NH$_4$NO$_3$ | 400 |
| | MgSO$_4$•7H$_2$O | 180.54 |
| | MnSO$_4$•4H$_2$O | 22.3 |
| | ZnSO$_4$•7H$_2$O | 8.6 |
| | CuSO$_4$•5H$_2$O | 0.25 |
| | CaCl$_2$•2H$_2$O | 72.5 |
| | K$_2$SO$_4$ | 990 |
| | Na$_2$MoO$_4$•2H$_2$O | 0.25 |
| | H$_3$BO$_3$ | 6.2 |
| | KH$_2$PO$_4$ | 170 |
| | FeNaEDTA | 36.7 |
| Vitamin | Myo-inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 75 |
| | Proline | 115 |
| Hormone | α-Naphtalene acetic acid | 2 |
| Sucrose | | 30,000 |

Meanwhile, the embryo- and needle-derived callus were also cultured in medium 2 of Table 2 and were compared with the procambium- and cambium-derived cell lines of the present invention.

The degree of aggregation of the cells was observed with biological microscope CX31 (Olympus, Japan). As a result, as shown in Table 3 below, it was observed that more than 90% of cells of the cell lines according to the present invention were present as single cells during suspension culture. As shown in FIG. 1(c), it was observed that the cells were morphologically characterized by a large number of the vacuoles and were in an undifferentiated state. The arrowed part in FIG. 1(c) indicates vacuoles in the *Taxus* procambium-derived cells.

TABLE 3

The type of cell aggregates of *Taxus* long-term cultures

| Large cell aggregates | Moderate cell aggregates | Small cell aggregates | Single cell population | Explant source |
|---|---|---|---|---|
| 60% | 30% | 7% | 3% | embryo needle |
| 0 | 0 | 9% | 91% | cambium |
| 0 | 0 | 7.4% | 92.6% | procambium |

Large cell aggregates, size higher than 1.5 × 10$^3$ μm;
Moderate cell aggregates 1 × 10$^3$ μm;
Small cell aggregates 4 × 10$^2$ μm < size < 1 × 10$^3$ μm Meanwhile, in order to examine the possibility of large scale cell culture, the embryo/needle-derived callus and the procambium- and cambium-derived cells were cultured in an airlift bioreactor (Sung-Won Cytec, Korea) having an internal volume of 3 L. The culture was carried out in the liquid medium of Table 2 under dark conditions at 25±1° C. As a result, it was observed that the doubling time of the embryo/needle-derived callus cultures was 12 days in the flask, but was 21 days in the bioreactor. It is believed that the cause is rapidly decreased cell viability due to the growth ring formation in the bioreactor, plant cell aggregation during culture, and the sensitivity to shear stress by rigid cell walls. Meanwhile, the doubling time of the *Taxus* procambium- and cambium-derived cell cultures according to the present invention was 4-5 days in the bioreactor, which did not differ from that in the flask or was shortened compared to that in the flask (Table 4). The procambium- and cambium-derived cell lines according to the present invention formed a very small growth ring area in the bioreactor, and the ring formed on the internal wall thereof was simply eliminated, when a simple stimulus was applied to the incubator to shake the medium. Also, it was shown that the inventive cell lines had low aggregation and contained a large number of vacuoles, and thus had low sensitivity to shear stress, such that cell viability did not decrease.

TABLE 4

| | Doubling time (day) | |
|---|---|---|
| Explant source | flask | bioreactor |
| embryo | 11.5 | 21 |
| needle | 12 | 21 |
| cambium | 5 | 4 |
| procambium | 5 | 4 |

(5) Treatment with Sugar and Methyl Jasmonate

The cell lines, which have been suspension-cultured for 14 days as described in Example 1-(4), were cultured in media (containing sterile water, 3-5 wt % (g/L) of raw sugar and 100 μM of methyl jasmonate) for 10 days under dark conditions, and then the cells were collected and used in the subsequent experiments.

Example 2

Preparation of Extract of Procambium- or Cambium-Derived Cell Line (1) Preparation of DMSO (dimethyl sulfoxide) Extract (i) 500 g of the cell line from which the medium has been removed were dissolved in 500 ml of DMSO with stirring at 50° C. for 6 hours.

(ii) After completion of the dissolution, the cell solution was centrifuged at 3,000 g for 10 minutes, and the supernatant was collected, thus obtaining a DMSO-soluble substance.

(iii) The obtained DMSO-soluble substance was concentrated using a rotary vacuum concentrator.

(iv) The concentrated sample was dried using a freeze dryer, thereby obtaining a DMSO extract.

Figure 2:
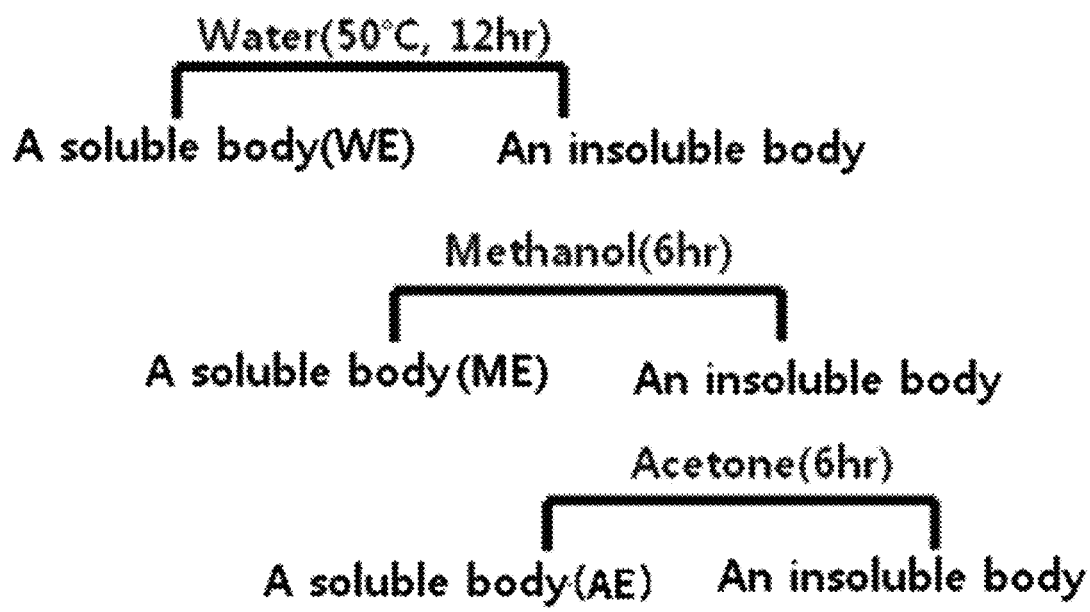
FIG. 2 is a flow chart showing a process of extracting effective substances stepwise from the cell line according to the present invention.

(2) Preparation of Distilled Water Extract, Methanol Extract and Acetone Extract From the cell line prepared in Example 1, active substances were extracted stepwise as follows (FIG. 2).

(i) 500 g of the cell line from which the culture medium has been removed was dissolved in 500 ml of distilled water with stirring at 50° C. for 6 hours.

(ii) After completion of the dissolution, the cell solution was centrifuged at 3,000 g for 10 minutes, and the supernatant was collected, thus obtaining a distilled water-soluble substance.

(iii) After obtaining the distilled water-soluble substance, the remaining distilled water-insoluble substance was dissolved in 500 ml of methanol with stirring at room temperature for 6 hours.

(iv) After completion of the dissolution, the solution was centrifuged at 3,000 g for 10 minutes, and the supernatant was collected, thus obtaining a methanol-soluble substance.

(v) After obtaining the methanol-soluble substance, the remaining methanol-soluble substance was dissolved in 500 ml of acetone with stirring at room temperature for 6 hours.

(vi) After completion of the dissolution, the solution was centrifuged at 3,000 g for 10 minutes, and the supernatant was collected, thus obtaining an acetone-soluble substance.

(vii) The distilled water-, methanol- and acetone-soluble substances obtained as described above were concentrated using a rotary vacuum concentrator.

(viii) The concentrated samples were dried using a freeze dryer and dissolved in distilled water, methanol and acetone, thereby obtaining a distilled water extract, a methanol extract and an acetone extract.

Example 3

Culture of Human Diploid Fibroblasts (HDF)

HDF cells were isolated from the fetal penis prepuce and cultured. The culture medium was prepared by adding 10% fetal bovine serum (FBS, Hyclone, Logan, Utah, USA) inactivated by heating at 56° C. for 30 minutes, 100 unit/ml of penicillin, 100 μg g/ml of streptomycin and 300 μg/ml of glutamine to DMEM medium (Invitroge Gibco life tech. Vienna, Austria). The cells were cultured in the medium, described above, in a 5% $CO_2$ incubator at a temperature of 37° C. and a humidity of 95% and subcultured at 3-4-day intervals, immediately before the cells were fused with each other. The subcultured cells were divided, according to the number of subcultures (passages), into young cells cultured less than 20 passages, middle cells cultured for 21-49 passages, and aged cells cultured more than 50 passages. The cultured cells were used in the experiments of Examples 4 to 6.

Example 4

Measurement of Antioxidant Activity of *Taxus* Cambium- or Procambium-Derived Cell Line Extract (1)—Measurement of Reactive Oxygen Species Induced by $H_2O_2$ In order to measure the antioxidant activity of the cambium- or procambium-derived cell line, the following test was carried out. Specifically, in order to examine whether reactive oxygen species induced by $H_2O_2$ are inhibited when the skin diploid fibroblasts (HDF cells) are treated with the distilled water extract among the extracts obtained in Example 2, the measurement of reactive oxygen species (ROS) was carried out.

The measurement of intracellular reactive oxygen species was carried out by Facscan analysis using a DCFDA (2',7'-dichlorofluorescin diacetate, Fluka Cat 35847 Molecular Probes, USA) fluorescent dye sensitive to reactive oxygen species. HDF cells according to each PD were grown on a 100-mm plate, and then incubated with 5 μM of DCFDA under dark conditions at 37° C. for 30 minutes. Then, the cells were washed twice with PBS and collected by treatment with trypsin-EDTA. Then, the cells were collected by centrifugation at 900 rpm for 4 minutes, and reactive oxygen species per 10,000 cells were measured (FIGS. 3(a) and 3(b)).

$5 \times 10^5$ cells were dispensed into a 6-well plate, and then treated with $H_2O_2$ alone or in combination with the extract obtained in Example 2. As the extract, the distilled water extract among the extracts obtained in Example 2 was used at a concentration of 10-100 μg/ml, preferably 50 μg/ml. Then, the cells were washed 2-3 times with HBSS (Hank's balanced salt solution) and stabilized in HBSS for about 30 minutes. Then, the cells were stained with 10 μM of DCFDA (Molecular Probes USA) under dark conditions at 37° C. for 1 hour, washed three times with HBSS, and then observed with a fluorescence microscope (FIG. 3(c)).

As described above, the HDF cells were treated with 200 μM of $H_2O_2$ and 10-100 μg/ml (preferably 50 μg/ml) of the distilled water extract obtained in Example 2, and the variation in the morphology of the cells was observed.

At 24 hours after the treatment of the cells with $H_2O_2$, the HDF cells generate reactive oxygen species (ROS) by oxidative stress. Because non-fluorescent DCFDA is oxidized by reactive oxygen species to form DCF showing strong fluorescence, reactive oxygen species can be measured. In this Example, FACS Calibur (Becton Dickinson Analytic Flow Cytometer, USA) was used for measurement.

Figure 3:
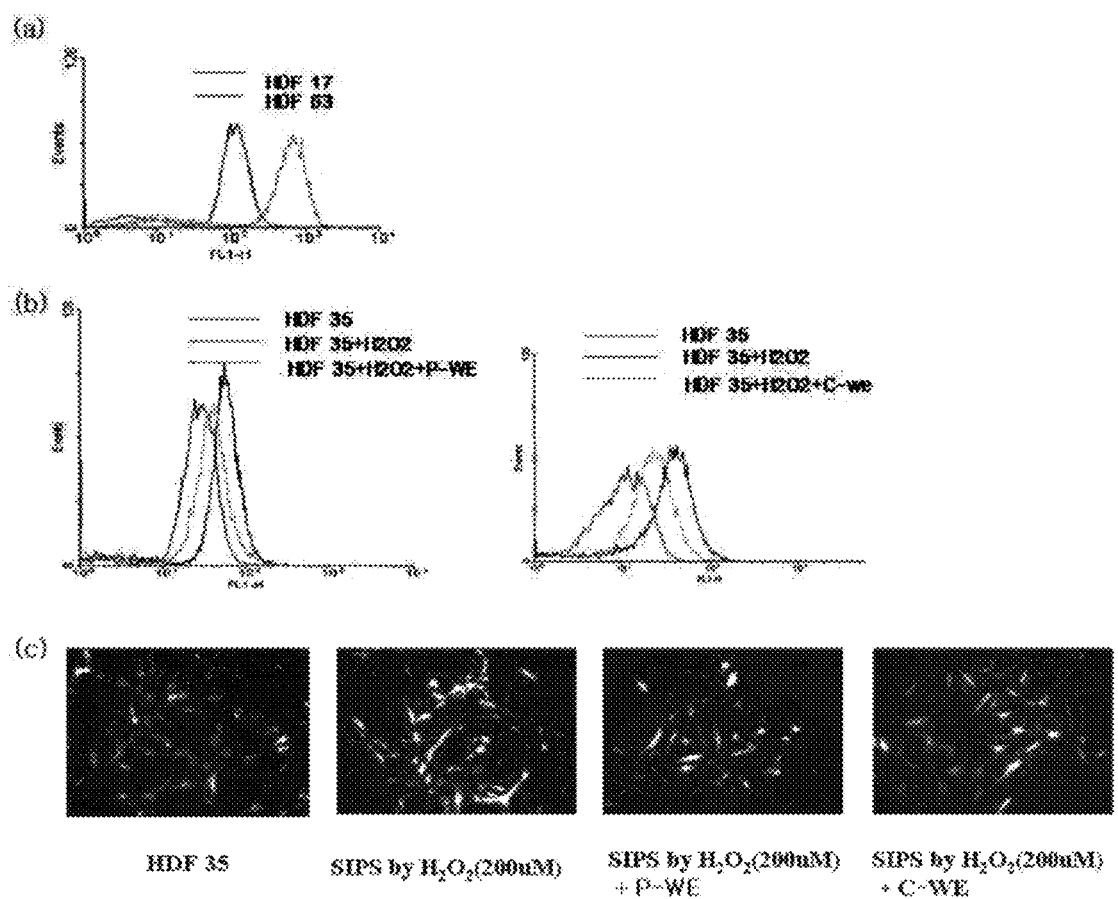
FIG. 3 depicts comparative graphs of ROS amount and DCFH fluorescence images, which show the antioxidant activity of cell line extracts according to the present invention, when the aging of human diploid fibroblasts (HDFs) is induced by treatment with $H_2O_2$ (p-WE: distilled water extract of procambium; C-WE: distilled water extract of cambium).

As a result, as shown in FIG. 3, the *Taxus* cambium-derived cell line extract and the *Taxus* procambium-derived cell line extract all inhibited the production of reactive oxygen species (ROS) (P-WE: distilled water extract of procambium, and C-WE:

distilled water extract of cambium in FIG. 3). Namely, it was observed that the two cell line extracts all inhibited the production of reactive oxygen species.

Example 5

Measurement of *Taxus* Cambium- or Procambium-Derived Cell Line Extract (2)—Measurement of Ability to Inhibit p-ERK½ Induced by $H_2O_2$ and Measurement of Ability to Induce MnSOD 5-1. Effect of *Taxus* Cambium- or Procambium Cell Line Extract on the Inhibition of Expression of p-ERK½

It is known that the expression of p-ERK½ is increased by reactive oxygen species in vivo. Thus, in order to examine whether the cell line extract according to the present invention inhibits the expression of p-ERK½, HDK cells were treated with the cell line extract obtained in Example 2 together with $H_2O_2$.

HDF cells were treated with 200 μM of $H_2O_2$ and the cell line-distilled water extract obtained in Example 2, and after 11 days, the cells were collected, and a protein was extracted from the cells. The protein was quantified by a Bradford assay. Namely, after collecting the HDF, the intracellular protein was extracted and quantified.

p-ERK½ was quantified by Western blotting. Specifically, the quantified protein was mixed with bromophenol blue dye solution, and then subjected to 10% SDS-polyacrylamide gel electrophoresis (SDS-PAGE). After the electrophoresis, the protein was transferred to a polyvinylidene fluoride membrane (Millipore) and immersed in 0.5% skim milk-containing TBS (Tris buffered saline)-tween solution (10 mM Tris HCl, 100 mM NaCl, 0.1% Tween 20, pH 7.5) to block nonspecific reactions.

Then, the membrane was allowed to react with a 1:600 dilution of an anti-rabbit antibody (Upstate) for ERK at room temperature for 3 hours, and then with anti-rabbit IgG antibody as secondary antibody. After completion of the reaction, the membrane was washed four times with TBS (Tris buffered saline)-tween solution, and allowed to react with ECL (enhanced chemiluminescence) detection reagent for 1 minute, and then exposed to an X-ray film at room temperature.

Figure 4:
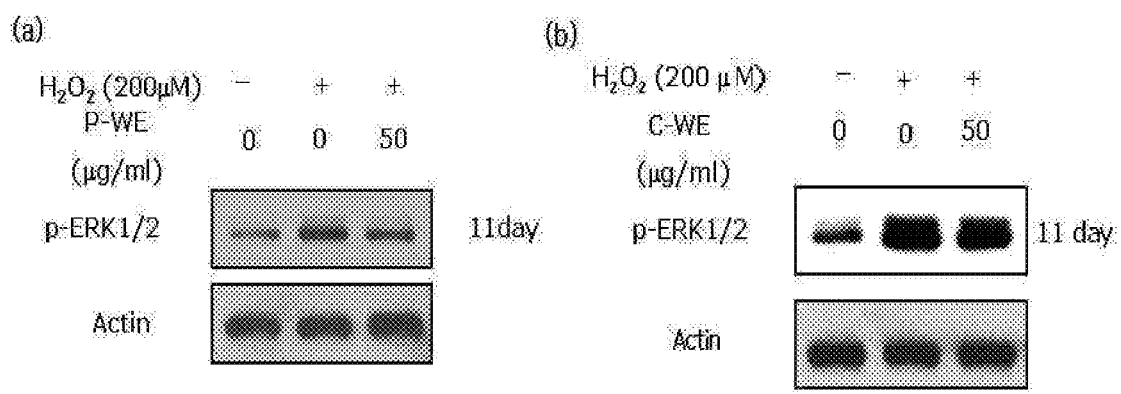
FIG. 4 is a set of photographs, which show the ERK expression inhibitory ability of cell line extracts according to the present invention, when the aging of human diploid fibroblasts (HDFs) is induced by treatment with $H_2O_2$ (p-WE: distilled water extract of procambium; C-WE: distilled water extract of cambium).

As a result, as shown in FIG. 4, it was observed that the expression of p-ERK½ was lower in the test group treated with $H_2O_2$ together with the cell line extract than in the control group treated with $H_2O_2$ alone.

5-2. Effect of *Taxus* Cambium- or Procambium-Derived Cell Line Extract on the Induction of Expression of MnSOD It is known that the expression of MnSOD is increased by reactive oxygen species in vivo. Thus, in order to examine whether the cell line extract according to the present invention induces the expression of MnSOD, HDK cells were treated with $H_2O_2$ and the cell line extract obtained in Example 2.

HDF cells were treated with 200 μM of $H_2O_2$ and the distilled water extract of the cell line obtained in Example 2, and after 3, 7 and 11 days, the cells were collected and a protein was extracted from the cells. The protein was quantified by a Bradford assay. Namely, the HDF cells were collected, and then the intracellular protein was extracted and quantified.

MnSOD was quantified by Western blotting. Specifically, the quantified protein was mixed with bromophenol blue dye solution and then subjected to 10% SDS-polyacrylamide gel electrophoresis (SDS-PAGE). After the electrophoresis, the protein was transferred to a polyvinylidene fluoride membrane (Millipore) and immersed in 0.5% skim milk-containing TBS (Tris buffered saline)-tween solution (10 mM Tris. HCl, 100 mM NaCl, 0.1% Tween 20, pH 7.5) to block nonspecific reactions.

Then, the membrane was allowed with a 1:600 dilution of anti-mouse antibody for MnSOD at room temperature for 3 hours, and then with anti-mouse IgG antibody as secondary antibody. After completion of the reaction, the membrane was washed 4 times with TBS (Tris buffered saline)-tween solution, and allowed to react with ECL (enhanced chemiluminescence) detection reagent for 1 minute, and then exposed to an X-ray film at room temperature.

Figure 5:
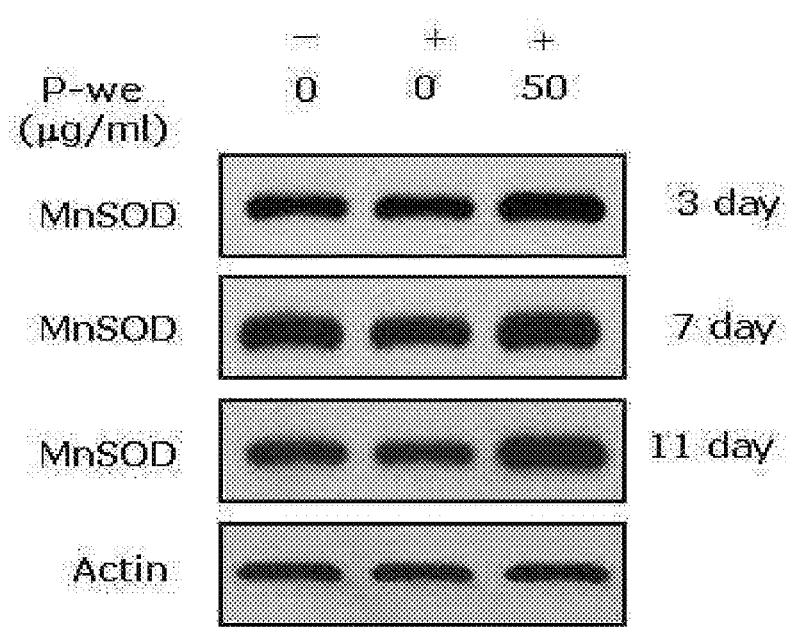
FIG. 5 is a set of photographs, which show the MnSOD expression-inducing ability of cell line extracts according to the present invention, when the aging of human diploid fibroblasts (HDFs) is induced by treatment with $H_2O_2$ (p-WE: distilled water extract of procambium).

As a result, as shown in FIG. 5, the signal of MnSOD was increased in the test group treated with $H_2O_2$ together with the cell line extract of the present invention compared to the control group treated with $H_2O_2$ alone.

Example 6

Measurement of Anti-Inflammatory Activity of *Taxus* Cambium- or Procambium-Derived Cell Line Extract—Ability to Inhibit CAM-1, MMP-9, MMP-2 and IL-1β Induced by LPS LPS (Lipopolysacharide: *Escherichia coli* strain B5:025, Sigma, St. Louis, Mo.) extracted from *E. coli* toxin induces the activation of nuclear factor-κB (NF-κB) in the nuclei of cells, such as macrophages, fibroblasts, dendritic cells and lymphocytes, to stimulate the secretion of various inflammatory cytokines. It is known that, if cells with LPS, IL-1β, ICAM-1, MMP-9 and MMP-2 will be induced to stimulate inflammation. Thus, in order to examine whether the obtained cambium- or procambium-derived cell line extract inhibits the signals of such proteins, the following test was carried out.

6-1. Effect of *Taxus* Cambium- or Procambium-Derived Cell Line Extract on the Inhibition of Expression of IL-1β

It is known that, if cells are treated with LPS, the product IL-1β will be increased by inflammatory signal transduction. Thus, in order to examine whether the cell line extract according to the present invention inhibits the expression of IL-1β, HDK cells were treated with LPS and the cell line extract obtained in Example 2.

HDF cells were treated with 10 μg/ml of LPS and 10-100 μg/ml (preferably 50 μg/ml) of the methanol extract among the cell line extracts obtained in Example 2. 3, 6 and 24 hours after treatment with the methanol extract, the cells were collected and proteins were extracted from the cells. The proteins were quantified by a Bradford assay. Namely, the HDF cells were collected and then the intracellular proteins were extracted and quantified.

IL-1β was quantified by Western blotting. The quantified protein was mixed with bromophenol blue dye solution, and then subjected to 10% SDS-polyacrylamide gel electrophoresis (SDS-PAGE). After the electrophoresis, the protein was transferred to a polyvinylidene fluoride membrane (Millipore) and immersed in 0.5% skim milk-containing TBS (Tris buffered saline)-tween solution (10 mM Tris. HCl, 100 mM NaCl, 0.1% Tween 20, pH 7.5) to block nonspecific reactions.

Then, the membrane was allowed to react with a 1:600 dilution of anti-mouse antibody for IL-1β at room temperature for 3 hours, and then with anti-mouse IgG antibody as secondary antibody. After completion of the reaction, the membrane was washed 4 times with TBS (Tris buffered saline)-tween solution, and allowed to react with ECL (enhanced chemiluminescence) detection reagent for 1 minute, and then exposed to an X-ray film at room temperature.

Figure 6:
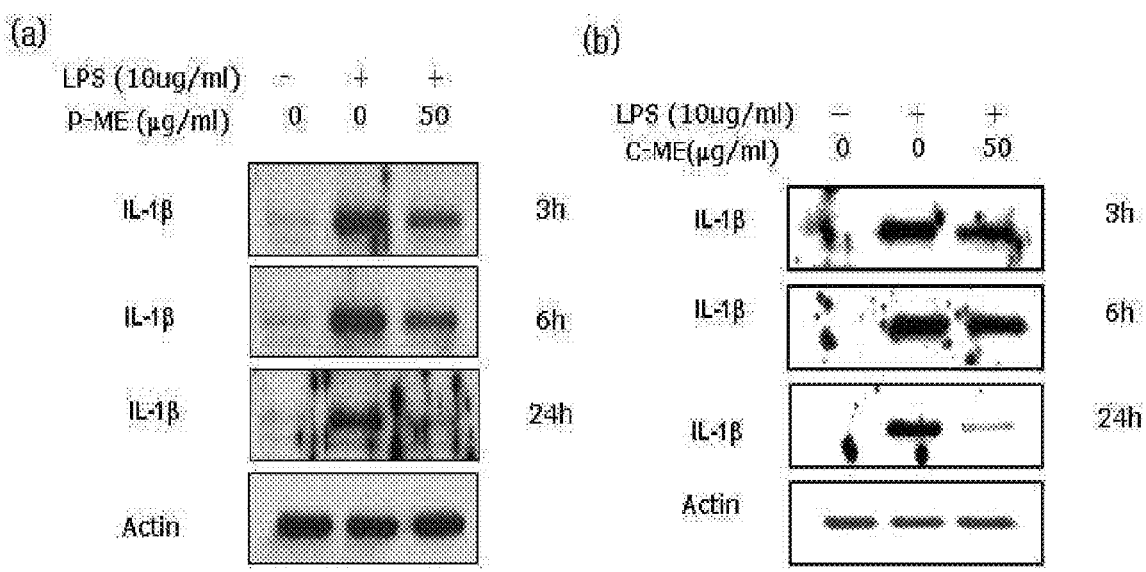
FIG. 6 is a set of photographs, which show the IL-1β expression inhibitory ability of cell line extracts according to the present invention, when human diploid fibroblasts (HDFs) are treated with LPS to induce inflammation (P-ME: methanol extract of procambium; C-ME: methanol extract of cambium).

As a result, as shown in FIG. 6, it could be seen that the signal of IL-1β was reduced in the test group treated with LPS together with the cell line extract of the present invention compared to in the control group treated with LPS alone.

6-2. Effect of *Taxus* Cambium- or Procambium-Derived Cell Line Extract on the Inhibition of Expression of MMP-9

It is known that, if cells are treated with LPS, the product MMP-9 will be increased by inflammatory signal transduction.

Thus, in order to examine whether the cell line extract according to the present invention inhibits the expression of MMP-9, HDK cells were treated with LPS and the cell line extract obtained in Example 2.

HDF cells were treated with 10 μg/ml of LPS and 10-100 μg/ml (preferably 50 μg/ml) of the methanol extract among the extracts obtained in Example 2. 6 hours after treatment with the methanol extract, the cells were collected and a protein was extracted from the cells. The protein was quantified by a Bradford assay. Namely, the HDF cells were collected, and then the intracellular protein was extracted and quantified.

MMP-9 was quantified by Western blotting. Specifically, the quantified protein was mixed with bromophenol blue dye solution, and then subjected to 10% SDS-polyacrylamide gel electrophoresis (SDS-PAGE). After the electrophoresis, the protein was transferred to a polyvinylidene fluoride membrane (Millipore) and immersed in 0.5% skim milk-containing TBS (Tris buffered saline)-tween solution (10 mM Tris. HCl, 100 mM NaCl, 0.1% Tween 20, pH 7.5) to block nonspecific reactions.

Then, the membrane was allowed to react with a 1:600 dilution of anti-mouse antibody (Upstate) for MMP-9 at room temperature for 3 hours, and then with anti-mouse IgG antibody as secondary antibody. After completion of the reaction, the membrane was washed 4 times with TBS (Tris buffered saline)-tween solution, and allowed to react with ECL (enhanced chemiluminescence) detection reagent for 1 minute, and then exposed to an X-ray film at room temperature.

Figure 7:
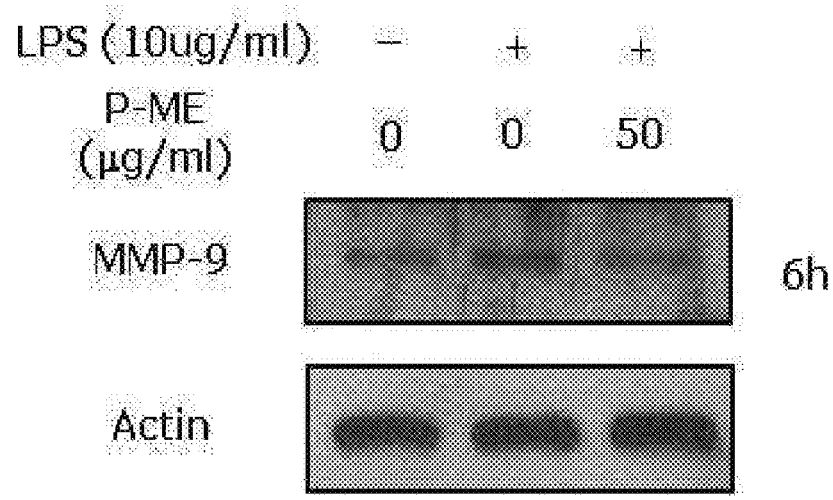
FIG. 7 is a set of photographs, which show the MMP-9 expression inhibitory ability of cell line extracts according to the present invention, when human diploid fibroblasts (HDFs) are treated with LPS to induce inflammation (P-ME: methanol extract of procambium).

As a result, as shown in FIG. 7, it was observed that the signal of MMP-9 was reduced in the test group treated with LPS together with the cell line extract of the present invention compared to in the control group treated with LPS alone.

6-3. Effect of *Taxus* Cambium- or Procambium-Derived Cell Line Extract on the Inhibition of Expression of MMP-2

It is known that, if cells are treated with LPS, the product MMP-2 will be increased by inflammatory signal transduction.

Thus, in order to examine whether the cell line extract according to the present invention inhibits the expression of MMP-2, HDK cells were treated with LPS and the cell line extract obtained in Example 2.

HDF cells were treated with 10 μg/ml of LPS and 10~100 μg/ml (preferably 50 μg/ml) of the methanol extract among the extracts obtained in Example 2. In 3, 6 and 24 hours after treatment with the methanol extract, the cells were collected and a protein was extracted from the cells. The protein was quantified by a Bradford assay. Namely, the HDF cells were collected, and then the intracellular protein was extracted and quantified.

MMP-2 was quantified by Western blotting. Specifically, the quantified protein was mixed with bromophenol blue dye solution, and then subjected to 10% SDS-polyacrylamide gel electrophoresis (SDS-PAGE). After the electrophoresis, the protein was transferred to a polyvinylidene fluoride membrane (Millipore) and immersed in 0.5% skim milk-containing TBS (Tris buffered saline)-tween solution (10 mM Tris. HCl, 100 mM NaCl, 0.1% Tween 20, pH 7.5) to block nonspecific reactions.

Then, the membrane was allowed to react with a 1:600 dilution of mouse antibody (Upstate) for MMP-2 at room temperature for 3 hours, and then with anti-mouse IgG antibody as secondary antibody. After completion of the reaction, the membrane was washed 4 times with TBS (Tris buffered saline)-tween solution, and allowed to react with ECL (enhanced chemiluminescence) detection reagent for 1 minute, and then exposed to an X-ray film at room temperature.

Figure 8:
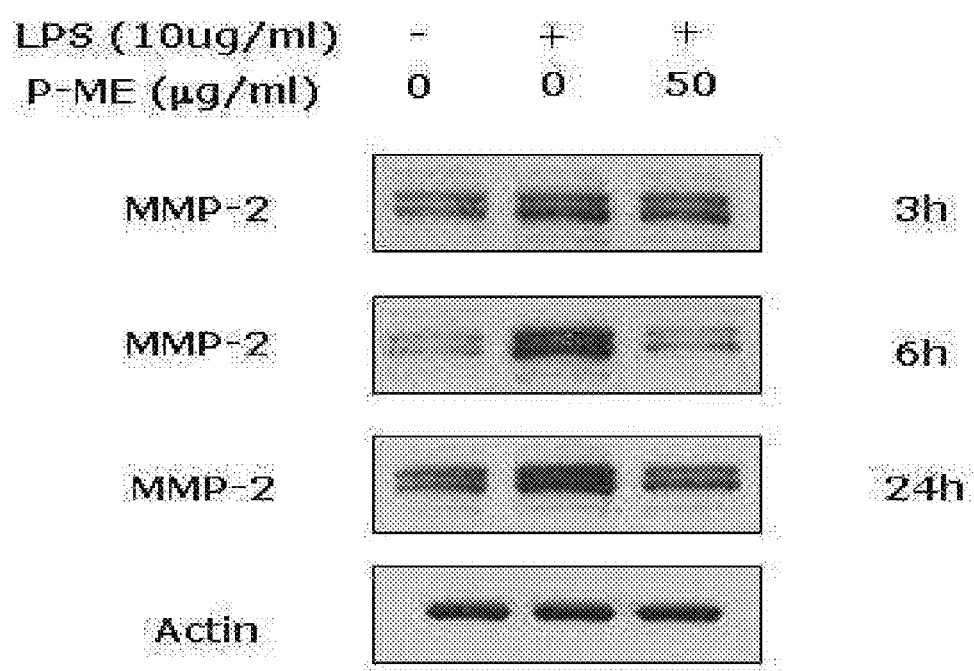
FIG. 8 is a set of photographs, which show the MMP-2 expression inhibitory ability of cell line extracts according to the present invention, when human diploid fibroblasts (HDFs) are treated with LPS to induce inflammation (P-ME: methanol extract of procambium).

As a result, as shown in FIG. 8, it could be seen that the signal of MMP-2 was reduced in the test group treated with LPS together with the cell line extract of the present invention compared to in the control group treated with LPS alone.

6-4. Effect of *Taxus* Cambium- or Procambium-Derived Cell Line Extract on the Inhibition of Expression of ICAM-1

In order to examine whether the cell line extract according to the present invention inhibits the expression of ICAM-1, HDK cells were treated with LPS and the cell line extract obtained in Example 2.

HDF cells were treated with 10 μg/ml of LPS and 10~100 μg/ml (preferably 50 μg/ml) of the methanol extract among the extracts obtained in Example 2. In 1, 3, 6, 12 and 24 hours after treatment with the methanol extract, the cells were collected and a protein was extracted from the cells. The protein was quantified by a Bradford assay. Namely, the HDF cells were collected, and then the intracellular protein was extracted and quantified.

ICAM-1 was quantified by Western blotting. Specifically, the quantified protein was mixed with bromophenol blue dye solution, and then subjected to 10% SDS-polyacrylamide gel electrophoresis (SDS-PAGE). After the electrophoresis, the protein was transferred to a polyvinylidene fluoride membrane (Millipore) and immersed in 0.5% skim milk-containing TBS (Tris buffered saline)-tween solution (10 mM Tris. HCl, 100 mM NaCl, 0.1% Tween 20, pH 7.5) to block nonspecific reactions.

Then, the membrane was allowed to react with a 1:600 dilution of mouse antibody (Upstate) for ICAM-1 at room temperature for 3 hours, and then with anti-mouse IgG antibody as secondary antibody. After completion of the reaction, the membrane was washed 4 times with TBS (Tris buffered saline)-tween solution, and allowed to react with ECL (enhanced chemiluminescence) detection reagent for 1 minute, and then exposed to an X-ray film at room temperature.

Figure 9:
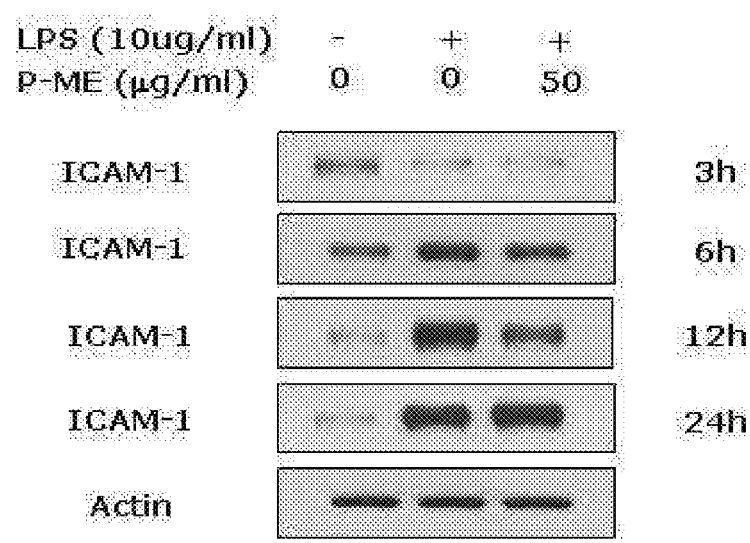
FIG. 9 is a set of photographs, which show the ICAM-1 expression inhibitory ability of cell line extracts according to the present invention, when human diploid fibroblasts (HDFs) are treated with LPS to induce inflammation (P-ME: methanol extract of procambium).

As a result, as shown in FIG. 9, it could be seen that the signal of ICAM-1 was reduced in the test group treated with LPS together with the cell line extract of the present invention compared to in the control group treated with LPS alone.

ICAM-1 is a typical protein of cell adhesion molecule group expressed on the surface of endothelial cells. Normally, it is expressed in a very low level; however, when it is stimulated by inflammation-mediating molecules of cytokines such as TNF-α, interferon-γ, and interleukin-1β, the level of expression is accelerated rapidly to play a role in adhering inflammatory cells such as monocytes or lymphocytes that move in blood and in moving the inflammatory cells to the inflammation-occurrence tissues [Wegner C. D. et al, *Science,* 247(1941):456, 1990; Dustin, M. L. et al, *J. Immunol.,* 137(1):245, 1986]. Therefore, the expression of ICAM-1 plays an important role in the amplification of inflammation when inflammatory cells move and gather on the inflammation-occurrence regions at its early stage. Thus, it was shown that treatment with the cell line according to the present invention inhibited the expression of ICAM-1, suggesting that the composition according to the present invention has the effects of inhibiting and preventing inflammation.

Example 7

Cytotoxicity Test

In order to examine whether the *Taxus* cambium- or procambium-derived cell line is cytotoxic, the following test was carried out.

Normal human diploid fibroblasts (NHDF; purchased from MCTT, Korea) were cultured in 10% FBS-containing DMEM medium (Welgene, Korea). The fibroblasts were seeded into a 96-well plate at a density of $1 \times 10^4$ cells per well and cultured for 12 hours. Then, FBS-free DMEM medium was treated for 24 hours with each of 1 ppm, 10 ppm and 100 ppm of the DMSO extract of the *Taxus* cambium-derived cell line obtained in Example 2 or with each of 1, 5 and 10 vol % of the culture medium obtained by removing the cell line therefrom in Example 2. A control group (N) was not treated with the sample. The viability of the fibroblasts was determined by culturing the cells for 2 hours in FBS-free DMEM medium containing 10% WST-1 solution and then measuring the absorbance at 450 nm.

Figure 10:
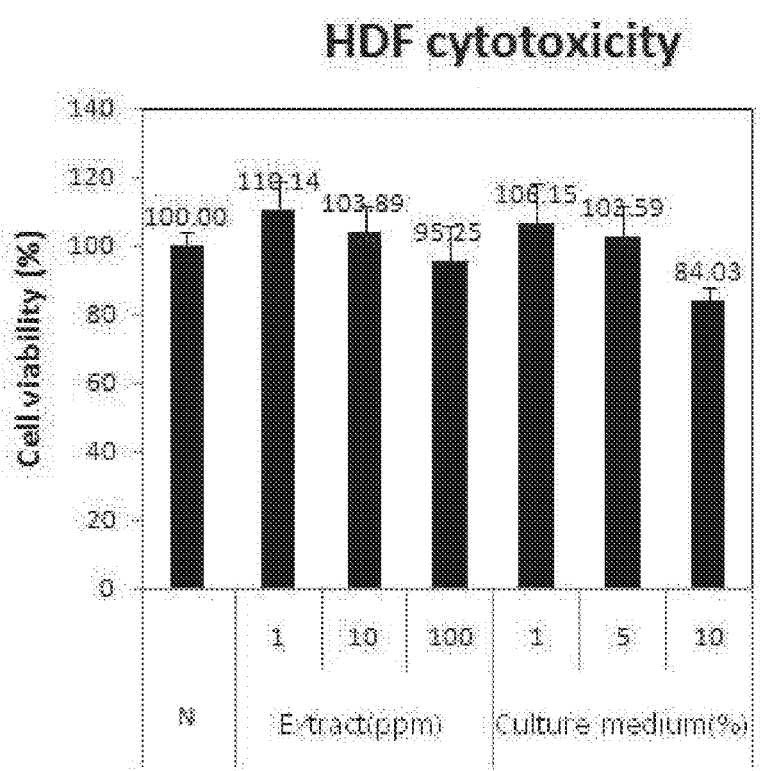
FIG. 10 is a graphic diagram showing the results of measuring the viability of fibroblasts treated with a cell line extract according to the present invention (DMSO extract of a *Taxus* cambium-derived cell line).

As a result, as shown in FIG. 10, the DMSO extract of the *Taxus* cambium-derived cell line did not reduce the cell viability in the concentration range used, and the culture medium slightly reduced the cell viability at a concentration of 10 vol %. Because a substance showing a cell viability of less than 80% is considered to be cytotoxic, it was confirmed that the cell line extract and culture medium according to the present invention were not cytotoxic in the concentration ranges used.

Example 8

Examination of Effect on the Removal of Reactive Oxygen Species Generated by UV Irradiation In order to measure the antioxidant activity and anti-aging activity of the *Taxus* cambium- or procambium-derived cell line according to the present invention, the following test was carried out.

First, human keratinocyte (HaCaT; German Cancer Research Institute, Heidelberg, Germany) were cultured in 10% FBS-containing DMEM medium. The cells were seeded into a 96-well plate at a density of $3 \times 10^4$ cells per well and cultured for 12 hours to adhere to the culture plate. Also, FBS-free DMEM medium was treated for 3 hours with each of 1, 10, 25 and 50 ppm of the DMSO extract of the *Taxus* cambium- and procambium-derived cell lines of Example 2 or with each of 0.1 and 1 vol % of the culture medium of Example 2. Also, a positive control group was treated with 10 nM of NAC (N-acetyl-cysteine), and an additional control group was treated with each of 1, 10, 25 and 50 ppm of a DMSO extract of *Taxus*.

Then, the cells were washed with HBSS buffer and cultured with 50 μM DCF-DA (HBSS) at 37° C. for 20 minutes. The cells were washed twice again with HBSS buffer, 30 μl HBSS was added thereto, and the cells were irradiated with UV light at a dose of 200 mJ/cm² at 365 nm. After culturing the cells 37° C. for 2 hours, the fluorescence of the cells was measured (excitation: 485 nm; emission: 535 nm; Infinite M-200, Tecan), and by using WST-1 solution the cell viability was measured and corrected. The effects of the samples on the removal of reactive oxygen species were evaluated by comparing the fluorescence of the UV-irradiated group with the fluorescence of the UV-non-irradiated group taken as 100.

Figure 11:
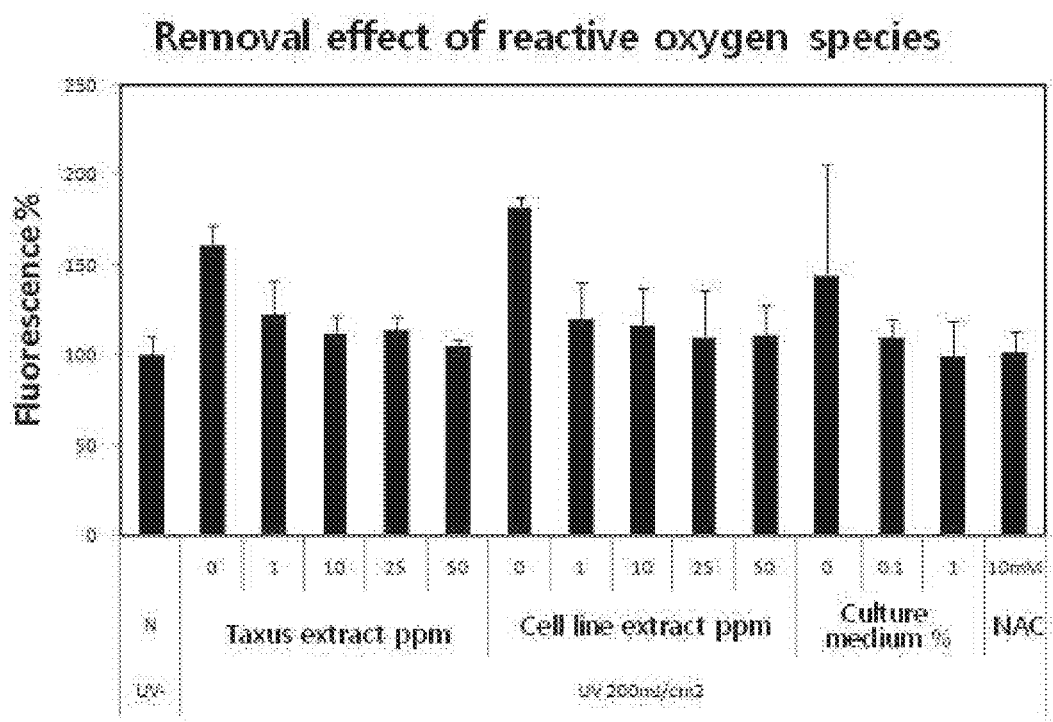
FIG. 11 is a graphic diagram showing the effects of the removal of reactive oxygen species which are generated by irradiation with UV light in a cell line extract and culture medium of the present invention.

As a result, as can be seen in FIG. 11, the DMSO extract and culture medium of the cell line according to the present invention had the effect of removing reactive oxygen species induced by UV light (in the case of the cell line extract, the values measured for the procambium-derived cell line extract and the cambium-derived cell line extract were recorded as average values). Particularly, in the case in which the cells were treated with the *Taxus* extract as the control group and irradiated with UV light, the fluorescence values were decreased by 44% (1 ppm), 55% (10 ppm), 48% (25 ppm) and 56% (50 ppm) compared to that of the group not treated with the sample (0 ppm), whereas in the case of the cell line extract according to the present invention, the fluorescence values were significantly decreased by 62% (1 ppm), 70% (10 ppm), 73% (25 ppm), 70% (50 ppm) compared to that of the group not treated with the sample (0 ppm). This suggests that the cell line according to the present invention has a much more potent antioxidant effect compared to *Taxus*.

Example 9

Examination of Effect on the Inhibition of Collagenase (MMP-1) Production Induced by UV Irradiation In order to measure the anti-aging activity of the *Taxus* cambium- or procambium-derived cell line according to the present invention, the following test was carried out.

First, fibroblasts (MCTT, Korea) were seeded into a 24-well plate at a density of $2 \times 10^4$ cells per well and cultured for 12 hours to adhere to the culture plate. Then, the cells were starved in FBS-free DMEM medium for 12 hours. The cells were washed with DPBS buffer and irradiated with UV light at a dose of 100 mJ/cm² at 365 nm. Also, the DMEM medium was treated for 24 hours with each of 50 or 25 ppm of the DMSO extract of the *Taxus* cambium- and procambium-derived cell line of Example 2 or with each of 1 and 0.1 vol % of the culture medium of Example 2. Also, a positive control group was treated with 1 μM RA (retinoic acid), and an additional group was treated with 50 and 25 ppm of a *Taxus* extract. Then, the medium was collected and centrifuged, and the amount of MMP-1 in the supernatant was quantified by an ELISA (Amersham) assay. By using WST-1 solution, the cell viability was measured and corrected.

Figure 12:
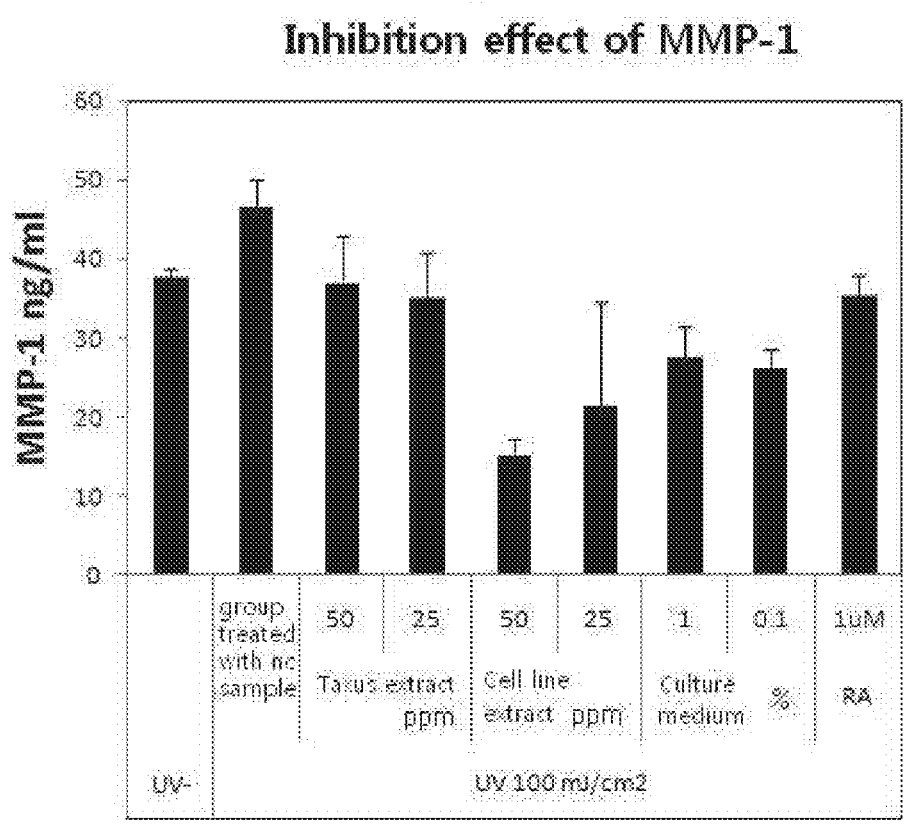
FIG. 12 is a graphic diagram showing the effects of the inhibition of MMP-1 production in a cell line extract and culture medium of the present invention when MMP-1 is induced by irradiation with UV light.

As a result, as shown in FIG. 12, the cell line extract and cell line culture medium according to the present invention showed an excellent of inhibiting MMP-1 production (in the case of the cell line extract, the values measured for the procambium-derived cell line extract and the cambium-derived cell line extract were recorded as average values). Particularly, the cell line extract and cell line culture medium according to the present invention showed an excellent effect on the inhibition of MMP-1 compared to the control group *Taxus* extract and RA known to have an excellent anti-aging effect, suggesting that they are particularly useful as anti-aging cosmetic compositions.

Example 10

Effect on the Inhibition of Intracellular Melanogenesis

In order to measure the whitening activity of the *Taxus* cambium- or procambium-derived cell line, the following test was carried out.

First, murine melanoma cells (B-16 F1) (Korea Cell Line Bank, Korea) were added to 10% FBS-containing DMEM medium in a 6-well plate at a density of $1 \times 10^5$ cells per well, and then cultured under conditions of 5% $CO_2$ and 37° C. until about 80% of the cells were attached to the well bottom. Then, the medium was replaced with a medium containing each of 1 and 10 ppm of the DMSO extract of the *Taxus* cambium- and procambium-derived cell lines prepared in Example 2 or with each of 0.05, 0.1 and 1 vol % of the culture medium of example 2, and the cells were cultured under 5% $CO_2$ and 37° C. for a given time. Also, a positive control group was treated with 1 mM kojic acid, and a negative control group (control group in FIG. 13) was not treated with the sample. The cells from which the medium has been removed was washed with PBS and collected by treatment with trypsin. The cell pellets were added to 100 μl 1M NaOH containing 10% DMSO, thus obtaining intracellular melanin. The solution was measured for absorbance at 490 nm using a microplate reader (Tecan Infinite M200, Austria), and the amount of melanin per protein was calculated. The protein was quantified by a Bradford assay.

Figure 13:
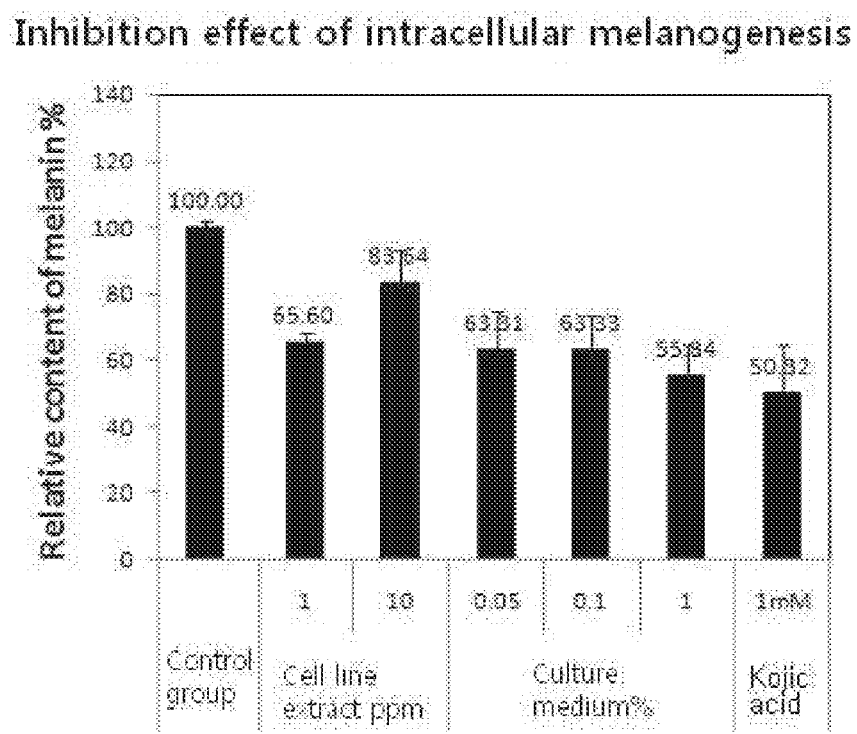
FIG. 13 is a graphic diagram showing the effects of the inhibition of melanogenesis in the B-16 melanoma cell line of a cell line extract and culture medium of the present invention.

As a result, as can be seen in FIG. 13, the cell line extract and culture medium according to the present invention inhibited melanogenesis (in the case of the cell line extract, the values measured for the procambium-derived cell line extract and the cambium-derived cell line extract were recorded as average values). Particularly, when the cells were treated with 1 ppm of the cell line extract or the culture medium, a melanogenesis inhibitory effect substantially similar to that of kojic acid known to have a whitening effect could be obtained, suggesting that the cell line extract and culture medium according to the present invention are very useful as whitening cosmetic compositions.

Example 11

Preparation of Pharmaceutical Formulations

Formulation 1: Preparation of Tablet 100 mg of the cell line extract prepared in Example 2 was mixed with 100 mg of maize starch, 100 mg of lactose and 2 mg of magnesium stearate, and the mixture was compressed into a tablet according to a conventional tableting method.

Formulation 2: Preparation of Capsule Formulation 500 mg of the cell line extract prepared in Example 2 was filled in a soft gelatin capsule to prepare a capsule formulation.

Formulation 3: Preparation of Syrup Formulation 1 g of the cell line prepared in Example 1 was mixed with 10 g of isomerized sugar, 5 g of mannitol and a suitable amount of purified water, and the mixture was prepared into 100 ml of a syrup formulation according to a conventional method.

Formulation 4: Preparation of Injection Solution 200 mg of the cell line extract prepared in Example 2 was heated and dissolved in 200 mg of physiological saline containing polyoxyethylene hydrogenated castor oil, thus preparing an injection solution containing the extract at a concentration of 0.1%.

Example 12

Preparation of Functional Food: Preparation of Functional Beverage

Preparation 1

200 mg of the cell line prepared in Example 1 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Preparation 2

200 mg of the cell line extract prepared in Example 2 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Example 13

Preparation of Functional Cosmetic Products

Preparation 1: Milk Lotion

A milk lotion having the following composition was prepared according to a conventional method: 6.2 mg of the cell line extract prepared in Example 2, 6.5 mg of 1,3-butylene glycol, 1.2 mg of glycerin, 0.2 mg of D-panthenol, 0.3 mg of ethanol, 0.1 mg of carbomer, 1.5 mg of stearic acid, 0.7 mg of polysorbate 60, 0.6 mg of lipophilic glyceryl stearate, 0.3 mg of sorbitan sesquioleate, 0.6 mg of cetearyl alcohol, 3.5 mg of squalane, 3 mg of caprylic/capric triglyceride, 0.4 mg of dimethicone, a small amount of a preservative, a suitable amount of compound fragrance, and purified water (amount that makes a total of 100 mg).

Preparation 2: Cream

A cream having the following composition was prepared according to a conventional method: 5.0 mg of the cell line extract prepared in Example 2, 7.0 mg of 1,3-butylene glycol, 1.0 mg of glycerin, 0.1 mg of D-panthenol, 0.4 mg of magnesium aluminosilicate, 2.0 mg of stearic acid, 1.5 mg of polysorbate 60, 2.0 mg of lipophilic glyceryl stearate, 1.5 mg of sorbitan sesquioleate, 4.0 mg of mineral oil, 3.0 mg of cetearyl alcohol, 3.8 mg of squalane, 2.8 mg of caprylic/capric triglyceride, 0.4 mg of dimethicone, a suitable amount of xanthan gum, a suitable amount of triethanolamine, a suitable amount of tocopherol acetate, a small amount of a preservative, a suitable amount of compound fragrance, and purified water (amount that makes a total of 100 mg).

INDUSTRIAL APPLICABILITY

As described above, the composition according to the present invention has minimized side effects compared to existing antioxidants and anti-inflammatory agents, is involved in intracellular metabolism to reduce intracellular reactive oxygen species, and reduces and induces aging-related signals. Thus, the composition of the preset invention is useful for preventing and delaying aging. In addition, the composition of the present invention has the effect of inhibiting melanogenesis, and thus is useful as a whitening cosmetic composition.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of inhibiting inflammation, skin oxidation, and/or skin aging in a subject in need thereof, the method comprising
   administering to said subject an effective amount of a composition comprising an extract of a *Taxus* cell line, wherein the extract is produced by:
   (i) dissolving 500 g of a *Taxus* cambium- or procambium cell line in 500 mL of DMSO with stirring at 50° C. for 6 hours to obtain a dissolved product; and
   (ii) centrifuging the dissolved product obtained in step (i) at 3000 g for 10 minutes and collecting the supernatant, wherein the supernatant is said extract.

2. The method according to claim 1, wherein the cell line has the characteristic that it is in an innately undifferentiated state, separated from the callus formed by dedifferentiation, and is present as single cells during suspension culture.

3. The method according to claim 1, wherein the cell line is obtained using an isolation method comprising the following steps of:
   (a) obtaining a *Taxus* cambium- or procambium-containing tissue;
   (b) culturing the obtained *Taxus* cambium- or procambium-containing tissue to induce a cambium or procambium layer proliferated from the cambium or procambium and an amorphous callus layer proliferated from tissues other than the cambium or procambium; and (c) isolating the cambium or procambium layer from the callus layer, and collecting a *Taxus* cambium- or procambium cell line from the cambium or procambium layer.

4. The method according to claim 3, wherein the cell line is additionally cultured in a medium, which contains 3-5 wt % of raw sugar or sugar; and/or at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate.

5. The method according to claim 2, wherein the cell line is obtained using an isolation method comprising the following steps of:
(a) obtaining a *Taxus* cambium- or procambium-containing tissue;
(b) culturing the obtained *Taxus* cambium- or procambium-containing tissue to induce a cambium or procambium layer proliferated from the cambium or procambium and an amorphous callus layer proliferated from tissues other than the cambium or procambium; and
(c) isolating the cambium or procambium layer from the callus layer, and collecting a *Taxus* cambium- or procambium cell line from the cambium or procambium layer.

6. The method according to claim 5, wherein the cell line is additionally cultured in a medium, which contains 3-5 wt % of raw sugar or sugar; and/or at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate.

7. A method of inhibiting inflammation, reducing skin aging and/or reducing wrinkles in a subject in need thereof, the method comprising
applying to said subject an effective amount of a composition comprising an extract of a *Taxus* cell line, wherein the extract is produced by:
(i) dissolving 500 g of a *Taxus* cambium- or procambium cell line in 500 mL of DMSO with stirring at 50° C. for 6 hours to obtain a dissolved product; and
(ii) centrifuging the dissolved product obtained in step (i) at 3000 g for 10 minutes and collecting the supernatant, wherein the supernatant is said extract.

8. The method according to claim 7, wherein the cell line has the characteristic that it is in an innately undifferentiated state, separated from the callus formed by dedifferentiation, and is present as single cells during suspension culture.

9. The method according to claim 8, wherein the composition inhibits the production of MMP-1.

10. The method according to claim 8, wherein the cell line is obtained using an isolation method comprising the following steps of:
(a) obtaining a *Taxus* cambium- or procambium-containing tissue;
(b) culturing the obtained *Taxus* cambium- or procambium-containing tissue to induce a cambium or procambium layer proliferated from the cambium or procambium and an amorphous callus layer proliferated from tissues other than the cambium or procambium; and
(c) isolating the cambium or procambium layer from the callus layer, and collecting a *Taxus* species cambium- or procambium cell line from the cambium or procambium layer.

11. The method according to claim 10, wherein the cell line is additionally cultured in a medium, which contains 3-5 wt % of raw sugar or sugar; and/or at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate.

12. The method according to claim 7, wherein the composition inhibits the production of MMP-1.

13. The method according to claim 7, wherein the cell line is obtained using an isolation method comprising the following steps of:
(a) obtaining a *Taxus* cambium- or procambium-containing tissue;
(b) culturing the obtained *Taxus* cambium- or procambium-containing tissue to induce a cambium or procambium layer proliferated from the cambium or procambium and an amorphous callus layer proliferated from tissues other than the cambium or procambium; and
(c) isolating the cambium or procambium layer from the callus layer, and collecting a *Taxus* species cambium- or procambium cell line from the cambium or procambium layer.

14. The method according to claim 13, wherein the cell line is additionally cultured in a medium, which contains 3-5 wt % of raw sugar or sugar; and/or at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate.

15. A method of whitening a skin area of a subject in need thereof, the method comprising applying to the skin area of said subject
an effective amount of a composition comprising an extract of a *Taxus* cell line, wherein the extract is produced by:
(i) dissolving 500 g of a *Taxus* cambium- or procambium cell line in 500 mL of DMSO with stirring at 50° C. for 6 hours to obtain a dissolved product; and
(ii) centrifuging the dissolved product obtained in step (i) at 3000 g for 10 minutes and collecting the supernatant, wherein the supernatant is said extract.

16. A method of inhibiting skin aging in a subject in need thereof, the method comprising
orally administering to said subject an effective amount of a composition comprising an extract of a *Taxus* cell line, wherein the extract is produced by:
(i) dissolving 500 g of a *Taxus* cambium- or procambium cell line in 500 mL of DMSO with stirring at 50° C. for 6 hours to obtain a dissolved product; and (ii) centrifuging the dissolved product obtained in step (i) at 3000 g for 10 minutes and collecting the supernatant, wherein the supernatant is said extract.

* * * * *

UNITED STATES PATENT AND TRADEMARK OFFICE
CERTIFICATE OF CORRECTION

PATENT NO. : 9,585,923 B2
APPLICATION NO. : 12/992810
DATED : March 7, 2017
INVENTOR(S) : Lee et al.

Page 1 of 1

It is certified that error appears in the above-identified patent and that said Letters Patent is hereby corrected as shown below:

In the Claims

Column 24, Line 5: "callus layer, and collecting a Taxus species cambium-" to -- callus layer, and collecting a Taxus cambium- --

Column 24, Line 33: "callus layer, and collecting a Taxus species cambium-" to -- callus layer, and collecting a Taxus cambium- --

Signed and Sealed this
Second Day of May, 2017

Michelle K. Lee
*Director of the United States Patent and Trademark Office*